United States Patent [19]

Hargis et al.

[11] 3,965,080

[45] June 22, 1976

[54] POLYMERIZATION OF MONOMERS WITH ALKALINE EARTH METAL ORGANOMETALLIC COMPOUNDS

[75] Inventors: Ivan Glen Hargis, Tallmadge; Russell Anthony Livigni, Akron, both of Ohio

[73] Assignee: The General Tire & Rubber Company, Akron, Ohio

[22] Filed: Feb. 27, 1975

[21] Appl. No.: 553,716

Related U.S. Application Data

[60] Division of Ser. No. 328,583, Feb. 1, 1973, Pat. No. 3,928,302, which is a continuation-in-part of Ser. No. 69,476, Sept. 3, 1970.

[52] U.S. Cl. .......................... 526/183; 252/431 R; 260/859 R; 260/880 B; 260/888; 526/193; 526/204; 526/209; 526/217; 526/328; 526/335; 526/341; 526/346
[51] Int. Cl.$^2$ .................... C08F 1/28; C08D 1/18; C08F 3/76
[58] Field of Search ............. 260/94.2 R, 94.2 M, 260/94.6, 93.5 R, 93.5 S, 88.7 E, 86.1 R, 86.7, 85.5 ES, 85.5 HC, 85.5 L, 82.3, 83.5, 83.7

[56] References Cited

UNITED STATES PATENTS

| | | | |
|---|---|---|---|
| 3,041,312 | 6/1962 | Boyd | 260/47 |
| 3,509,067 | 4/1970 | Bostick | 260/665 |
| 3,526,604 | 9/1970 | Wadsworth | 260/2 |
| 3,548,033 | 12/1970 | Bostick | 260/879 |

*Primary Examiner*—Christopher A. Henderson, Jr.

[57] ABSTRACT

Organometallic compounds of high carbanion yield are prepared by metallation with barium, strontium or calcium or mixture of the same of certain acidic organic compounds having a pKa value of between about 15 and 35 on the MSAD scale in the presence of aprotic polar solvents, e.g., barium reacted with xanthene in 1,2-dimethoxyethane to yield dixanthenyl barium. Such organometallic compounds formed by metal-hydrogen exchange reaction are useful in initiating anionic growth-type polymerization of monomers, e.g., alkylene oxides and vinyl compounds, to form homopolymers and copolymers. The persistence of polymer carbanions created by such catalysts makes possible the controlled preparation of a variety of polymers, including block copolymers.

16 Claims, No Drawings

POLYMERIZATION OF MONOMERS WITH ALKALINE EARTH METAL ORGANOMETALLIC COMPOUNDS

This application is a division of prior copending application Ser. No. 328,583, filed Feb. 1, 1973, now U.S. Pat. No. 3,928,302 granted Dec. 23, 1975, which is a continuation-in-part of prior copending application Ser. No. 69,476, filed Sept. 3, 1970.

BACKGROUND OF THE INVENTION

1. Field of the Invention

This invention relates to new organometallic compounds formed by direct metallation of weakly acidic organic compounds with barium, strontium and/or calcium metal in the presence of an aprotic polar solvent. The metallation reaction involves a metal-hydrogen exchange to create compounds in which metal is joined to an organic radical by an ionic carbon to metal bond. These compounds are highly active as polymerization catalysts in initiating anionic growth-type polymerization of various monomers, e.g., alkylene oxides, vinyl compounds or the like, to form homopolymers and copolymers.

2. Description of the Prior Art

It has long been known that organometallic compounds in which metal is joined to an organic radical through a carbon to metal bond, may be prepared by a variety of methods. The Grignard reagents constitute a historic example of this type of compound. Tetraethyl lead and aluminum alkyl compounds are other examples of organometallic compounds having carbon to metal bonds which can be prepared quite readily in good yield and purity. Actually, the ready availability of aluminum alkyls has prompted their use as starting materials for formation of more complex organometallic compounds (see U.S. Pat. No. 3,360,537). A metal alkyl such as zinc diethyl has been used in metal interchange reaction for the preparation of organometallic compounds of strontium (see Gilman et al., J.A.C.S., 65, 268–1943). Alkaline earth organo-metallic compounds formed in this manner were found to have low solubility in organic solvents such as benzene (see Gilman et al., J.A.C.S., 67, 520–1945).

It is known that some hydrocarbons possess carbon-hydrogen groups which exhibit ionic-like properties forming groups which are referred to as carbanions. Such hydrocarbons exhibit an acidic like property which is stronger in the case of some hydrocarbons than with others. This has resulted in the development of an acidity scale by which the relative ease with which the hydrocarbon forms a carbanion is characterized by a pKa value of a McEwen - Streitwieser - Applequist - Dessy (M.S.A.D.) scale (see "Fundamentals of Carbanion Chemistry" by Cram, p. 19, published 1965 by Academic Press). On this scale, the lower the pKa value for a hydrocarbon, the more acidic it is and the greater is the ease with which the hydrocarbon will form a carbanion.

Due to the highly basic nature and strong reactivity of alkali metals, formation of organometallic compounds of alkali metals with acidic type organic compounds can be readily accomplished. These can then be used in metal-hydrogen interchange reactions to form the corresponding organo-metallic compounds of other less reactive or less basic metals (see U.S. Pat. No. 3,450,728). Where it is desired to form organometallic compounds of less basic metals, e.g., alkaline earth metals, a technique for indirect metallation has been developed. Thus, by conducting a reaction of a metal with an acidic hydrocarbon in liquid ammonia as a reaction medium, calcium hexammoniate which forms between calcium and the liquid ammonia will react with an acidic hydrocarbon to form an organometallic compound (see U.S. Pat. No. 3,365,404).

Most aliphatic hydrocarbons do not have sufficient acidity to permit preparation of alkyl organometallic compounds from alkaline earth metals by direct metallation. Formation of such compounds by reaction of methyl iodide with barium, strontium or calcium has been conducted using pyridine as a reaction medium (see J.A.C.S., 80, 5324–1958).

Cyclopentadiene is a hydrocarbon exhibiting relatively high acidity, i.e., it possesses a pKa value on the MSAD scale of 15. However, the hydrocarbon is not sufficiently "acid" to react with strong bases such as sodium hydroxide although it will react directly with sodium metal. In order to produce the calcium adduct of cyclopentadiene, the hydrocarbon has been reacted with calcium carbide using liquid ammonia or certain amines as accelerators for the reaction (see U.S. Pat. No. 2,835,712). A similar technique has been used in the formation of other calcium metallo-organic compounds such as calcium adducts with triphenylmethane and fluorene (see U.S. Pat. No. 3,365,404).

Organometallic compounds are known to be useful as catalysts for polymerization of a variety of polymerizable monomers. Actually, such adducts of metals vary in catalytic activity depending upon the metal present in the compound, the method of preparation of the adduct and its possible association in complexes with other materials. Such catalytic materials are of great commercial significance because they provide unique catalytic procedures, e.g., stereospecific polymerizations of the Ziegler-Natta type. Al, Be, Ca, Mg and Zn amide-alcoholate compounds have, for example, been used to polymerize monomeric cyclic carbonates (see U.S. Pat. No. 3,301,824). The adduct of calcium with certain acidic aryl hydrocarbons and ammonia have been used for polymerization of epoxides (see U.S. Pat. No. 3,365,404). Epoxides have also been polymerized using complexes between organometallic compounds and alcohols (see U.S. Pat. No. 3,275,598), organometallic compounds and polyoxyalkylene glycols (see U.S. Pat. No. 3,427,259) or complexes of organometallic compounds with polar solvents (see U.S. Pat. No. 3,337,475). Also, barium and other group II-A metals have been treated with certain compounds like naphthalene to form radical ions or anions and used in the polymerization of isoprene, styrene and so forth. These barium compounds react as follows:

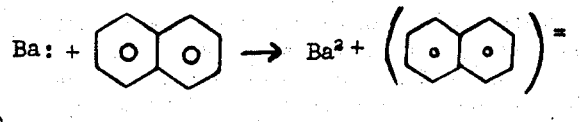

so that metallation of the naphthalene does not occur. Rather, complexes are formed by a transfer of electrons from the metal to the naphthalene which has a high electron affinity. See U.S. Pat. No. 3,509,067. The utility of organometallic compounds as catalysts in polymerization reactions and for other purposes would be further improved if organometallic compounds of alkaline earth metals could be created by less complicated procedures than available heretofore that would produce the organometallics in good yield and in a form in which the compound exhibits high carbanion content and catalytic activity.

OBJECTS

A principal object of this invention is the provision of new methods for producing organometallic compounds of alkaline earth metals. Further objects include the provision of:

1. new organometallic compounds of barium, calcium and/or strontium and certain acidic organic compounds;
2. new methods for the preparation of alkaline earth organometallic compounds by direct metallation of certain acidic organic compounds;
3. new catalytic materials useful in conducting homogeneous anionic polymerizations of vinyl compounds, oxirane compounds and other polymerizable monomers;
4. improvements in the art of making and using organometallic compounds;
5. new polymerization methods in which a polymer carbanion is formed exhibiting persistent qualities upon which monomers may grow to form controlled-structure block copolymers;
6. new methods for the production of organometallic compounds which function with relative ease to form desired products in high yield from readily available components;
7. organometallic compounds of alkaline earth metals exhibiting high solubility in aprotic polar solvents and non-polar hydrocarbons.
8. organometallic compounds having carbanion content sufficient to give relatively rapid rate of chain initiation with polymerizable monomers.

Other objects and further scope of applicability of the present invention will become apparent from the detailed description given hereinafter.

SUMMARY OF THE INVENTION

These objects are accomplished according to the present invention by a metal-hydrogen exchange reaction between barium, strontium or calcium metal and an acidic organic compound under substantially anhydrous conditions in the presence of an aprotic polar solvent. Advantageously, the metal is used in a finely divided state such as metal filings, and is employed in excess of the stoichiometric amount needed to react with the acidic compound. The formation of the organometallic compound is generally indicated by the appearance of a characteristic color associated with the formation of the carbanion. The resulting organometallic compounds contain a metal selected from the group consisting of barium, strontium and/or calcium in which the metal is joined to the organic moiety of the compound by an ionic carbon to metal bond. A preferred compound in accordance with the invention exhibiting unique polymerization catalytic activity is dixanthenyl barium. For example:

Here, a hydrogen atom from the organic compound is replaced with the metal.

The objects are further accomplished in accordance with the invention by compositions of matter useful as homogeneous anionic polymerization catalysts resulting from the aforesaid metallation reactions, which compositions comprise a solution in an aprotic polar solvent of an organometallic compound of an acidic organic compound having a pka value as measured in an aprotic solvent on the MSAD scale of from about 15 to 35 and a metal selected from the group consisting of barium, strontium, calcium and mixtures thereof, said metal being joined to the organic compound by an ionic carbon to metal bond.

The objects of the invention are further accomplished by polymerization of vinyl monomers, oxirane monomers or other polymerizable monomers by bringing the monomer into contact with a composition as aforesaid to form monomer organometallic adduct between a portion of the monomer and carbanion present in the catalytic composition, permitting further portions of monomer to grow onto such adduct and then terminating the resulting polymerization as desired. Such termination may be by addition of an active hydrogen compound such as an alcohol, an amine, water or other compound containing an active hydrogen permitting the added compound to combine with the growing polymer carbanion whereby further growth is terminated. Dixanthenyl barium or other organometallic compound in accordance with the invention, thus, creates a propagation center by reaction with polymerizable monomer from which active growth of further monomer portions proceeds in the absence of chain termination with progressive increase in molecular weight. Such active polymer metal gegenion is persistent in the absence of chain termination and permits dissimilar monomers to be added thereon to form block copolymers. By selection of the chain termination reagent, terminal functionality on the resulting polymers of block copolymers can be attained. For example, chain termination with epoxides or $CO_2$ provides polymer chains with terminal hydroxyl or carboxyl functionality. Such terminally functional polymers may be subsequently employed in post-polymerization reactions, e.g., reaction with polyisocyanates to form polyurethanes or polyamides.

The polymerizable vinyl monomers are those having an activated unsaturated double bond, for example, those monomers where adjacent to the double bond there is an electrophilic constituent (atom or radical) stronger than hydrogen and which is not easily removed by a strong base. Examples of such monomers are nitriles like acrylonitrile, methacrylonitrile; amides like acrylamide, methacrylamide; acrylates and alkacrylates like methyl acrylate, ethyl acrylate, butyl acrylate, ethyl hexyl acrylate, octyl acrylate, methyl methacrylate, ethl methacrylate, butyl methacrylate, methyl ethacrylate, ethyl ethacrylate, butyl ethacrylate, octyl ethacrylate, the Ba, Ca and Sr salts of the acrylic and alkacrylic acids such as acrylic, methacrylic and etha-

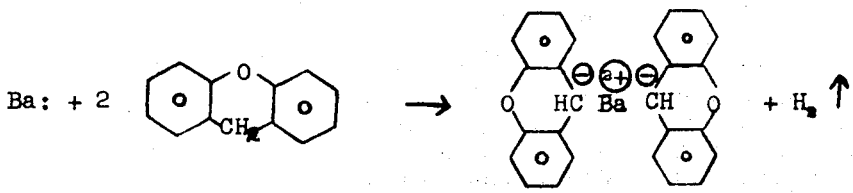

crylic acid; the dienes such as butadiene, chloroprene, isoprene and dimethyl butadiene; and the vinyl benzenes like styrene, meta vinyl toluene, and para vinyl toluene and the like and mixtures of the same. The polymerizable oxirane monomers are those of carbon, hydrogen and oxygen and having a ring of two carbon atoms and one oxygen and which will readily open and polymerize to form polyethers. Examples of oxirane monomers which can be employed are ethylene oxide, propylene oxide, butylene oxide, isobutylene oxide, allyl glycidyl ether, crotyl glycidyl ether, isoprene monoxide, butadiene monoxide, vinyl cyclohexene monoxide and the like and mixtures thereof. These monomers have up to 14 carbon atoms and are free of groups which would destroy the catalyst.

The invention provides, therefore, a process for the preparation of catalyst material active for the anionic polymerization of monomers by reacting a metal from the group consisting of barium, strontium and/or calcium in the presence of an aprotic polar solvent with xanthene or other acidic organic material as defined herein having a pKa value between 15 and 35 on the MSAD scale until an organometallic reaction product soluble in the solvent is formed.

The catalysts of this invention cannot only be used to make, for example, homopolymers, but also copolymers and block polymers. To illustrate, where dixanthenyl barium is XBaX, A is styrene, B is butadiene, and PO is propylene oxide, the following reactions can occur:

(1) $XBaX + 2nA \rightarrow XA_nBaA_nX$, generally a homopolymer;

(2) $XA_nBaA_nX + 2nB \rightarrow XA_nB_nBaB_nA_nX$, generally a block polymer;

(3) $XBaX + nA + nB \rightarrow X(...BABBAAA...)Ba(AABBAB....)X$ generally a copolymer or mixed polymerizate; and (4) $XBaX + 2nPO \rightarrow X(PO)_nBa(OP)_nX$.

Treatment of the homopolymer of (1) (and (2), (3) and/or (4)) with ROH where H is an acidic proton can result in a generally stoichiometric splitting of the polymer:

(5) $XA_nBaA_nX + 2 ROH \rightarrow Ba(OR)_2 + 2XA_nH$.

Treatment of the homopolymer of (1) (and (2), (3) and/or (4)) with coupling agents can maintain the chain length of the polymer obtained or provide long chain branching where the branches may be of the same or different polymeric chain characteristics. Examples of coupling agents are 1,2-dichloroethane, silicon tetrachloride, 2,2'2''-trichlorotriethylamine, maleic or phthalic anhydride, 
and other coupling agents and the like. For example, (6) $XA_nBaA_nX + ClCH_2CH_2CL \rightarrow BaCl_2 + XA_nCH_2CH_2A_nX$.

Different polymers can be treated with the coupling agents to get branches of different blocks.

Reaction of a polymer of the present invention with ethylene oxide (EO), propylene oxide or $CO_2$ and subsequent hydrolysis or ion exchange will provide a polymer having OH or COOH functionality.

(7) 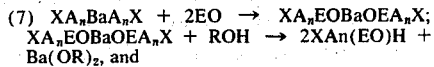
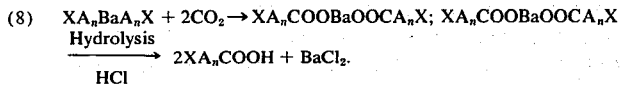

(8) $XA_nBaA_nX + 2CO_2 \rightarrow XA_nCOOBaOOCA_nX$; $XA_nCOOBaOOCA_nX$
$\xrightarrow[\text{HCl}]{\text{Hydrolysis}} 2XA_nCOOH + BaCl_2$.

DESCRIPTION OF PREFERRED EMBODIMENTS

The following examples will serve to illustrate the present invention with more particularity to those skilled in the art. In these examples and throughout the remaining specification and claims all parts and percentages are by weight unless otherwise specified. Also, in these examples all reactions and polymerizations were conducted in closed vessels under nitrogen or argon (inert atmosphere).

EXAMPLE 1 - PREPARATION OF DIXANTHENYL BARIUM

A solution was prepared by dissolving 91 parts of xanthene in 1200 parts of the dimethyl ether of ethylene glycol, also referred to as glyme. To this solution, 181 parts of barium metal filings were added. Reaction proceeded immediately to produce a blue-color solution which gradually changed to red. After one week, the soluble product solution was filtered from unreacted metal. The carbon-barium content was determined by radiochemical tritiation and found to be 0.13 meq/ml. This showed that 30% of the starting reagents were converted to metallo-organic compound in which barium was joined to xanthenyl radicals by carbon to metal bond. The remaining xanthene was converted to the barium salt of o-hydroxydiphenylmethane and a small amount of other unidentified byproduct.

In another case, direct metallation of xanthene with barium metal was attempted with the xanthene dissolved in hydrocarbon solvents, e.g., benzene. It was found that the xanthene could not be directly metallated in this manner with barium. However, it was found possible to obtain solutions of dixanthenyl barium in hydrocarbonaprotic polar solvent mixtures by solvent exchanging a portion of the aprotic polar solvent in which metallation was conducted with a hydrocarbon solvent. In one case, dixanthenyl barium soluble in a benzene-glyme mixture comprising 99.5% benzene was prepared in this fashion to contain approximately 0.016 meq/ml. in carbon-barium content.

The structure of the colored product was substantiated as dixanthenyl barium by (a) agreement of the visible spectrum of the organo-barium product, $\lambda$ max. = 464 m$\mu$, with the reported spectrum for xanthenyl lithium, $\lambda$ max. = 470 m$\mu$, and (b) carbonation of the reaction mixture to obtain xanthene-9-carboxylic acid (M.P. = 220°C.).

The carbanion content of the reaction product from barium metal and xanthene was 20–30% of the total alkalinity as determined by titration of the hydrolyzed product with standard acid. An analysis of the ether extract of the hydrolyzed reaction product by NMR, infrared and GLC (Gas-Liquid Chromatopgraphy)

procedures revealed the presence of a cleavage product of xanthene and a minor component believed to be hydrogenated xanthene. The cleavage product of xanthene was identified as o-hydroxydiphenylmethane resulting from C-O fission of the xanthene molecule. Assuming the catalyst or reaction mixture consisted only of dixanthenyl barium and the cleavage product, the total anion content agreed closely with that expected. Thus, the direct metallation of xanthene with barium in glyme produced a mixture of about 20 to 30% dixanthenyl barium and the remainder the barium salt of o-hydroxydiphenylmethane. By varying reaction time and intensity of stirring during metallation, total conversion of reactants to carbanion plus phenolate varied from 60 to 100% of starting materials. The cleavage product or salt does not appear to occur when metallating the other acidic organic compounds or in other aprotic solvents and/or at low temperatures.

EXAMPLE 2 - POLYMERIZATION OF STYRENE

Using as a catalyst the reaction mixture obtained in Example 1 of dixanthenyl barium and the barium salt of o-hydroxydiphenylmethane, styrene was converted almost quantitatively to polystyrene. Styrene (4.05 grams, 0.039 mole) was initiated with dixanthenyl barium (7.38 × 10$^{-4}$ of an equivalent, computed on dixanthenyl barium only) in 67 ml. of benzene/glyme mixture (15 vol % glyme) at room temperature (about 25°C). After a few hours, the conversion of monomer to polymer as 95%. Part of the resulting polystyrene was recovered by precipitation in methanol. Approximately 50% of the polystyrene chains were terminated with a phenolic group arising from chain transfer with the barium salt of o-hydroxydiphenylmethane. This salt, thus does not act as a catalyst or initiator but acts as a chain transfer agent to reduce the average molecular weight of the polymer obtained. The number average molecular weight as measured by vapor pressure osmometry, 2600, was less than the theoretical number average molecular weight of 5200 as calculated from the ratio of grams of monomer polymerized to moles of initiator present dixanthenyl barium

EXAMPLE 3 - POLYMERIZATION OF BUTADIENE

Butadiene (24.32 grams, 0.45 mole) was polymerized by dixanthenyl barium (1.05 × 10$^{-3}$ equiv.) in 86 ml of glyme, at room temperature, to produce 12.73 grams of polybutadiene after five days. The number average molecular weight was 1850 (VPO). The microstructure of the diene was shown by infrared to consist of 47% trans-1, 4 units, 26% cis-1, 4 units and 27% vinyl units.

In another case, butadiene (10.75 grams, 0.20 mole) initiated in 64 ml. of a benzene/glyme mixture (80 vol % benzene) with dixanthenyl barium (9.05 × 10$^{-4}$ equiv. in the 64 ml of solution) produced 10.10 grams of polybutadiene after four days at room temperature. Vapor pressure osmometry gave a number average molecular weight of 3000. The polymer contained 52% trans-1, 4 units, 26% cis-1, 4 units and 22% vinyl units.

EXAMPLE 4 - POLYMERIZATION OF METHYL METHACRYLATE

Methyl methacrylate (9.71 grams, 0.097 mole) was initiated with dixanthenyl barium (9.34 × 10$^{-4}$ equiv.) in 95 ml. of toluene/glyme mixture (87 vol % toluene) at −75°C. Polymerization was complete within a few minutes at −75°C. The polymer was dissolved in chloroform and precipitated in petroleum ether to give 8.6 grams of poly (methyl methacrylate).

EXAMPLE 5 - POLYMERIZATION OF PROPYLENE OXIDE

Propylene oxide (15.2 grams, 0.26 mole) was initiated with dixanthenyl barium (7.87 × 10$^{-4}$ equiv.) in 12 ml of glyme employing a high monomer concentration, 8.5 molar. Polymerization of three days at 50°C. followed by one day at 80°C. gave 6.0 grams of poly(-propylene oxide).

EXAMPLE 6 - BLOCK COPOLYMERIZATION

Using styrene as the monomer and the technique of incremental monomer addition, it was found that the polymerization of styrene proceeded in the absence of a chain termination reaction. Styrene (10.70 grams, 0.103 mole) was initiated with 5 ml of the living dixanthenyl polystyryl barium as described in Example 2 in 105 ml of a benzene/glyme mixture (99 vol % benzene) at room temperature. After one day, the conversion of monomer to polymer was 89%. The number average molecular weight as measured by membrane osmometry was 135,000. The theoretical molecular weight was calculated as 95,000.

Gel Permeation chromatograms on both polymers showed that the molecular weight of the polystyryl initiator was increased as evidenced by comparing the MWD's (molecular weight distributions) of the first block polymer and the final polymer. the MWD of the final polymer did not show the presence of the first block polymer, demonstrating that on addition of monomer, growth took place without chain termination. On the basis of these observations, it can be concluded that polymerization with an organo-metallic having an alkaline earth metal gegenion can be characterized as a termination-free anionic polymerization.

Unreacted xanthene, as well as the barium salt of o-hydroxydiphenylmethane, can participate in a chain transfer reaction with the propagating polymer chain. The effect of free xanthene to chain transfer was shown when xanthene was added to a polystyryl barium initiated polymerization of styrene (mole ratio of xanthene/initiator = 23). The molecular weight was decreased from $\overline{M}_n$ = 25,000 for a control polymerization without added xanthene to about 2000 for the final polymer.

Chain transfer to the barium salt of o-hydroxydiphenylmethane provides a fraction of the polymer chains with hydroxyl functionality. In one case, the phenol group was incorporated to the extent that 50% of the chains of a polystyrene, $\overline{M}_n$ = 2600, and 33% of the chains of a polybutadiene, $\overline{M}_n$ = 2900, were hydroxyl terminated.

EXAMPLE 7 - POLYBUTADIENE PREPARATIONS

A series of polymerizations of butadiene was made with organometallic barium compounds in several kinds of solvents and the resulting polybutadienes were subjected to microstructure analysis according to established procedure producing results as listed in the following table:

TABLE I

| Run | Initiator | Solvent | % Repeating Units | | |
|---|---|---|---|---|---|
| | | | cis-1,4 | trans-1,4 | vinyl |
| A | di (xanthenyl) Ba | Glyme | 26 | 47 | 27 |
| B | di (xanthenyl) Ba | Glyme/Benzene (80 vol % benzene) | 26 | 52 | 22 |

The foregoing results show that lower vinyl contents of polybutadiene are obtained using organo-metal initiators in accordance with the invention as compared with certain metal organo metallic initiators which lead to vinyl contents of 45% or greater, in the case of Na, K, Rb or Cs.

EXAMPLE 8 - PREPARATION OF DIXANTHENYL BARIUM IN HEXAMETHYLPHOSPHORAMIDE

Sixty parts of barium metal filings were reacted with 45.5 parts of xanthene dissolved in 534 parts of hexamethylphosphoramide (HMPA). The reaction mixture was stirred for 2 hours at 23°C. to form a blue-green color which gradually changed to a moderately intense red color after continued stirring at 23°C. for one day. The carbon-barium content, as determined by tritiation using hydroxyl tritiated propanol, was found to be 0.044 meq/gram solution, representing a 10% conversion of xanthene to metallo-organic compound. An analysis of the ether extract of the hydrolyzed reaction product by GLC did not reveal the presence of the cleavage product of xanthene. A quantitative yield of polystyrene resulted from the polymerization of styrene (4.0 g., 0.038 mole) with dixanthenyl barium ($2 \times 10^{-4}$ equiv.) in a mixture of HMPA and THF (72 vol % THF).

EXAMPLE 9 - PREPARATION OF DIXANTHENYL BARIUM IN HEXAMETHYLPHOSPHORAMIDE AT 80°C.

The procedure of Example 8 was repeated with the exception that after 2 hours at 23°C., the blue-green reaction mixture was reacted at 80°C. for 3 days. The color of the final solution was a very intense red. The carbon-barium content analyzed 0.24 meq/gram, demonstrating an almost six-fold increase in carbanion content as a result of the increased reaction temperature. The higher reaction temperature resulted in cleavage of a portion of the xanthene molecules to give a mixture of products, consisting of approximately 55% dixanthenyl barium and 45% of the barium salt of o-hydroxydiphenylmethane. Metallation in hexamethylphosphoramide at elevated temperatures permits metallation of weakly acidic hydrocarbons which do not react well at room temperature, an increase in yield of metallated compound, and a reduction in the time required for metallation.

EXAMPLE 10 - PREPARATION OF DIXANTHENYL STRONTIUM IN HEXAMETHYLPHOSPHORAMIDE AT 80°C.

Forty-nine parts of strontium metal filings were reacted with 45.5 parts of xanthene dissolved in 526 parts of HMPA. A lightly colored yellow green solution was formed after 3 days of stirring at 23°C. Further reaction at 80°C. for 3 days produced a red solution which analyzed for carbon-strontium content as 0.021 meq./gram. This value represented a conversion of 5% of the xanthene to dixanthenyl strontium.

The solution of dixanthenyl strontium was diluted with tetrahydrofuran and was used to initiate the polymerization of acrylonitrile at 23°C. Quantitative conversion to polyacrylonitrile occurred within a few minutes. The polymer was recovered by precipitation in methanol and separated by filtration to give a light yellow powder.

EXAMPLE 11 - PREPARATION OF DIINDENYL CALCIUM IN HEXAMETHYLPHOSPHORAMIDE AT 80°C.

Twenty parts of calcium metal filings were reacted with 32 parts of indene dissolved in 519 parts of HMPA. No reaction was apparent, from the lack of color formation after stirring for 3 days at 23°C. This reaction mixture was reacted at 80°C. for 3 days to produce a clear brown-orange solution. The carbon-calcium content of the reaction product was 0.0005 meq./gram.

Acrylonitrile (1.1 g., 0.02 mole) was initiated with diindenyl calcium ($5 \times 10^{-6}$ equiv.) in hexamethylphosphoramide. A considerable amount of heat was liberated upon addition of the initiator to monomer at 23°C. Polymerization occurred instantaneously to yield 1.0 g. of a yellow-white powder.

EXAMPLE 12 - PREPARATION OF DIINDENYL BARIUM IN HEXAMETHYLPHOSPHORAMIDE

Seventy parts of barium metal filings were reacted with 29 parts of indene in 535 parts of HMPA at 23°C. A yellow solution was initially formed after 2 hours of stirring. The reaction proceeded to produce an intense brown color after several days at 23°C. The carbon-barium content of the solution was 0.285 meq./g., representing a 65 conversion of indene to diindenyl barium.

Acrylonitrile (1.1 g., 0.02 mole) was polymerized with diindenyl barium in hexamethylphosphoramide at 23°C. Polymerization immediately followed with evolution of heat. Work-up of the reaction by precipitating in methanol, filtering out the polymer, washing with methanol and drying, gave 1.0 g. of a yellow-orange powder. The indene molecule was identified as part of the polyacrylonitrile chain by the infrared absorption at 670 $cm^{-1}$. This provides evidence for initiation by the indenyl anion.

EXAMPLE 13 - PREPARATION OF DI(TRIPHENYLMETHYL)BARIUM IN HEXAMETHYLPHOSPHORAMIDE

Seventy parts of barium metal filings were reacted with 61.1 parts of triphenylmethane in 531 parts of hexamethylphosphoramide. The reaction mixture was stirred at 23°C. for one day to produce a very slight color formation (light purple). Continuing the reaction at 80°C. for three days, gave an intensely red colored solution of di(triphenylmethyl)barium. The concentration of the resulting product was 0.04 meq./gram. Ten percent of the triphenylmethane was converted to metallo-organic compound.

EXAMPLE 14 - PREPARATION OF DI(DIPHENYLMETHYL)BARIUM IN HEXAMETHYLPHOSPHORAMIDE

Seventy-five parts of barium metal filings were reacted with 42.0 parts of diphenylmethane in 535 parts of hexamethylphosphoramide. A light yellow-green colored solution was formed after stirring at 23°C. for one day, indicative of only a small extent of conversion of the hydrocarbon to carbanion. After the reaction was allowed to continue at 80°C. for three days, an intense brown-orange solution was formed. Based on the carbon-barium content of the final product (0.06 meq./g.), 14% of the diphenylmethane was converted to di(diphenylmethyl)barium.

Styrene (1.0 gram, 0.0096 mole) was initiated with di(diphenylmethyl) barium (6 × $10^{-5}$ equiv.) at room temperature. After a few minutes at room temperature (about 25°C.), the resulting polystyrene (1.0 grams) was recovered by precipitation in methanol.

Examples of acidic organic compounds contemplated for use in accordance with the invention include: cyclopentadiene, indene, xanthene, 9-phenyl xanthene, triphenylmethane, acetylene, phenyl acetylene, 1,3,3-triphenyl propene, 9-phenyl fluorene, 9-(alpha naphthyl) fluorene, 9-(2-methoxy phenyl) fluorene, 9-(alpha naphthyl) xanthene, 9-(2-methoxy phenyl) xanthene, bis(2-methoxy phenyl) methane, 1,1,2-triphenyl ethane, 1,1-diphenyl alkanes in which the alkane group has 1 to 10 carbon atoms such as diphenyl methane and 1,1-diphenyl ethane, and the like and mixtures thereof. Excess metal over that required for metallation of the acidic organic compound is employed in the reaction to insure that it will go forward. Any metal remaining can be filtered from the solution. The metal is preferably in finely divided form to increase yield and reaction.

The success of metallation reactions in accordance with the invention is due to performing the metallations in the presence of an aprotic polar solvent. Dialkoxyalkanes, e.g., 1,2-dimethoxyethane; 1,3-diethoxypropane; 1,2-dipropoxyethane; etc., and dialkoxypolyoxyalkanes, e.g., bis-(2-methoxyethyl) ether, dimethyl ether of diethylene glycol, dimethylether of triethylene glycol, diethyl ether of dipropylene glycol, etc., peralkyl phosphoramides, e.g., hexamethyl phosphoramide; octamethyl pyrophosphoramide, etc., are preferred solvents for use in the new metallations. However, other aprotic polar solvents that may be used include the dialkyl ethers, e.g., diethyl ether, dihexyl ether, etc., peralkyl alkylene polyamines, e.g., N,N,N',N'-tetramethyl-ethylene diamine; N,N,N'-tetraethyl 1,3-propylene diamine, etc., and heterocyclic ethers, e.g., dioxane, tetrahydrofuran, etc. Mixtures of these solvents can be used. Such aprotic polar solvents may be used alone or in admixture with liquid hydrocarbons of pKa value of greater than about 35 on the MSAD scale, e.g., benzene, toluene, xylene, hexane, cyclohexane, etc. Such solvent mixtures may comprise 1–90% by weight hydrocarbon and preferably 5–25% hydrocarbon. In general, the maximum amount of catalyst concentration is about 1 mole of catalyst (or catalyst mixture) in 1 liter of the solvent. Moreover, mixtures of two or more of the aprotic polar solvents alone or mixed with the liquid hydrocarbon may be used. Operating temperatures for preparation of the catalysts range from about −90° to 150°C., preferably from about 20° to 100°C.

The preparation of organometallic compounds of alkaline earth metals in accordance with the invention proceed with relative ease to produce high yield of desired product from readily available components. The resulting products have solubility in both aprotic polar solvents and non-polar hydrocarbons. The organic metallic compounds exhibit high degree of ionic characteristics making them powerful initiators for relatively rapid rate of chain initiation with polymerizable monomers. Furthermore, the persistency in solution of the resulting polymer carbanions permits the new polymerization initiators and procedures to be used for production of block copolymers of controlled configuration and with selected terminal functionalities.

Temperatures during polymerization can vary from about −90° to 100°C. The amount of catalyst employed will vary with the type of polymer desired. For example, when making polymers having a high average molecular weight using a given amount of monomer and catalyst only a small amount of the catalyst is necessary whereas when making a low average molecular weight polymer larger amounts of catalyst are employed. Moreover, since the polymer is a living polymer, it will continue to grow as long as monomer is fed to the polymerization system. Thus, the molecular weight can be as high as a million, or even more.

The polymerization may be either a bulk (mass) or a solvent polymerization. In solvent polymerizations it is preferred to operate on a basis of not over about 15% polymer solids concentration in the solvent to enable ready heat transfer and processing. Solvents should be used which do not act as chain terminating agents. Polymerization should, of course, be conducted in a reactor fitted with a stirrer, heating and cooling means, means to pump in inert gas, monomer and catalyst, means to recover the polymer and so forth.

The polymers produced by the method of the present invention can be compounded and cured in the same manner as other plastic and rubber polymers. For example, they can be mixed with sulfur or sulfur furnishing materials, peroxides, carbon black, $SiO_2$, $TiO_2$, $Sb_2O_3$, red iron oxide, phthalocyanine blue or green, tetramethyl or ethyl thiuram disulfide, benzothiazyl disulfide and the like. Stabilizers, antioxidants, UV light absorbers and other antidegradants can be added to these polymers. They can also be blended with other polymers like natural rubber, butyl rubber, polyurethane elastomers and so forth.

The polymers produced by the method of the present invention can be used as paints, protective coatings for fabrics; in making fibers and textiles, body and engine mounts for automobiles, gaskets, tires, golf ball covers, foamed plastic insulation for buildings, tote boxes, electric wire and cable insulation; and as plasticizers and polymeric fillers for other plastics and rubbers.

The embodiments of the invention in which an exclusive property or privilege is claimed are defined as follows:

1. The method which comprises polymerizing at a temperature of from about −90° to 100°C. a polymerizable monomer selected from the group consisting of methyl acrylate, ethyl acrylate, butyl acrylate, ethyl hexyl acrylate, octyl acrylate, methyl methacrylate, ethyl methacrylate, butyl methyacrylate, methyl ethacrylate, ethyl ethacrylate, butyl ethacrylate, octyl ethacrylate, acrylonitrile, methacrylonitrile, butadiene, isoprene, dimethyl butadiene, styrene, metavinyl toluene and paravinyl toluene and mixtures of the same with at least one diorgano-metallic catalyst where the metal of said catalyst is selected from the group consisting of barium, strontium and calcium and mixtures thereof and where the organic moiety of said catalyst is selected from the group consisting of triphenyl methane, 1,3,3-triphenyl propene, bis(2-methoxy phenyl) methane, 1,1,2-triphenyl ethane, and 1,1-diphenyl alkanes in which the alkane group has from 1 to 10 carbon atoms and mixtures thereof, said metal being joined to said organic moiety by an ionic carbon to metal bond.

2. The method according to claim 1 where said catalyst comprises a solution in an aprotic polar solvent of said catalyst.

3. The method according to claim 2 in which the aprotic polar solvent is selected from the group consisting of dialkoxy alkanes, dialkoxy polyoxyalkanes, peralkyl phosphoramides, alkyl ethers, peralkyl alkylene polyamines and heterocyclic ethers and mixtures of the same.

4. The method according to claim 3 in which the aprotic solvent additionally contains a hydrocarbon solvent having a pKa value of greater than about 35 on the MSAD scale.

5. The method according to claim 1 in which the polymerization process is a solvent polymerization process, the monomer being used in an amount to provide a resulting polymer solids content of not greater than about 15% by weight in the solvent.

6. The method according to claim 1 in which the metal is calcium.

7. The method according to claim 1 in which the metal is strontium.

8. The method according to claim 1 in which the metal is barium.

9. The method according to claim 8 where the organic moiety is triphenyl methane.

10. The method according to claim 8 where the organic moiety is diphenyl methane.

11. The method according to claim 1 where the organic moiety is triphenyl methane.

12. The method according to claim 1 where the organic moiety is diphenyl methane.

13. The method which comprises polymerizing butadiene at a temperature of from about −90° to 100°C. with at least one catalyst selected from the group consisting of bis(diphenyl methyl) barium, bis(diphenyl methyl) strontium and bis(diphenyl methyl) calcium.

14. The method according to claim 13 where the catalyst is bis(diphenyl methyl) barium.

15. The method according to claim 8 where the organic moiety is 1,1-diphenylethane.

16. The method according to claim 1 where the organic moiety is 1,1-diphenylethane.

* * * * *